United States Patent
Wilkins et al.

(10) Patent No.: US 6,226,353 B1
(45) Date of Patent: May 1, 2001

(54) PHASE RETRIEVAL IN PHASE CONTRAST IMAGING

(75) Inventors: Stephen William Wilkins, Blackburn; Andrew Wesley Stevenson, Cranbourne; Peter Andrew Pogany, Glen Iris; Timur Gureyev, Chadstone, all of (AU)

(73) Assignee: X-Ray Technologies Pty, Ltd, Melbourne (AU)

( * ) Notice: Subject to any disclaimer, the term of this patent is extended or adjusted under 35 U.S.C. 154(b) by 0 days.

(21) Appl. No.: 09/331,861

(22) PCT Filed: Dec. 24, 1997

(86) PCT No.: PCT/AU97/00882

§ 371 Date: Sep. 13, 1999

§ 102(e) Date: Sep. 13, 1999

(87) PCT Pub. No.: WO98/28950

PCT Pub. Date: Jul. 2, 1998

(30) Foreign Application Priority Data

Dec. 24, 1996 (AU) .................................................. PO 4344
Sep. 5, 1997 (AU) .................................................. PO 8991

(51) Int. Cl.[7] ...................................................... H05G 1/00
(52) U.S. Cl. .................. 378/98.9; 378/98.11; 378/98.12
(58) Field of Search ............................... 378/98.9, 98.11, 378/98.12

(56) References Cited

U.S. PATENT DOCUMENTS

| | | | |
|---|---|---|---|
| 5,550,887 | * | 8/1996 | Schmal et al. .......................... 378/43 |
| 5,802,137 | * | 9/1998 | Wilkins .................................. 378/85 |
| 5,850,425 | * | 12/1998 | Wilkins .................................. 378/85 |
| 6,018,564 | * | 1/2000 | Wilkins .................................. 378/62 |

OTHER PUBLICATIONS

Pogany et al., Rev. Sci. Instrum. 68, 2774 (1997).*

* cited by examiner

Primary Examiner—David V. Bruce
Assistant Examiner—Allen C. Ho
(74) Attorney, Agent, or Firm—Fulwider Patton Lee & Utecht, LLP

(57) ABSTRACT

A method of obtaining in image of the phase change introduced by an object in penetrating radiation incident on the object includes irradiating the object with penetrating radiation having high lateral spatial coherence, and receiving at least a portion of the radiation at a detector after the radiation has merged from the object and thereby obtaining and storing at least two intensity records for the received radiation each including intensity values at predetermined intervals. These values are utilized to derive a grid of values defining an image of the phase change introduced by the object in the penetrating radiation. The intensity records are obtained at a uniform finite distance after the radiation has emerged from the object, and are for respective different energy distributions of the detected radiation. Apparatus is also disclosed.

41 Claims, 7 Drawing Sheets

PHASE RETRIEVAL IN PHASE CONTRAST IMAGING

FIELD OF THE INVENTION

This invention relates generally to the observation of structural features of objects utilising penetrating radiation such as x-rays. In particular, the invention relates to the derivation of images of the phase change introduced by an object in penetrating radiation incident on the object, from a two-dimensional intensity record of the penetrating radiation after it has traversed the object. The invention may be extended to retrieve separate phase and absorption data from a set of radiographic measurements.

BACKGROUND ART

The present applicant's international patent publications WO 95/05725 (PCT/AU94/00480) and WO 96/31098 (PCT/AU96/00178) disclose various configurations and conditions suitable for differential phase-contrast imaging using hard x-rays. Other earlier disclosures of interest are to be found in Soviet patent 1402871 and in U.S. Pat. No. 5,319,694. Differential phase-contrast imaging shows great promise for viewing the internal structure of objects for which traditional absorption-contrast radiography is of limited or no value because of very weak absorption contrast. This is the case, for example, with soft tissue within the human body.

The practical issue optimally and efficiently deriving the phase-contrast image for an object from the actual record at the detector is addressed in two related papers by Nugent et al *Phys. Rev. Lett.* 77, 2961–2964 (1996); *J. Opt. Soc. Am.* A13. 1670–82 (1996) and references therein. In these papers, it has been demonstrated that with monochromatic plane-wave x-radiation as in the configurations of WO 95/05725 and U.S. Pat. No. 5,319,694, the retrieval of phase information from measurement of the propagation of intensity can be used on treating the propagation of the modified radiation field whose characteristics reflect the phase modifying effects of the object. A two-dimensional recording of the intensity of the penetrating radiation after it has traversed the object is the result of variations in the local direction of propagation of the radiation arising from variations in local refractive index, typically an indication of a boundary or rapid variation in electron density within the object or of a thickness variation. The aforementioned articles by Nugent et al utilise a treatment of the propagation of a plane monochromatic electromagnetic wave on Maxwell's equations to derive a transport-of-intensity equation and propose solutions of this equation to derive a phase-contrast image from the intensity record. These suggested solutions to the transport-of-intensity equation involve expanding the phase in orthogonal functions. The kind of function chosen depends on the shape of the sample, and thus Zernike polynomials are adequate for a circular shape whilst a Fourier expansion is most suitable for a square-shaped sample.

The aforementioned international patent application WO 96/31098 discloses an in-line phase-contrast imaging configuration utilising a substantially point source and a two-dimensional x-ray imaging detector spaced from the object. It is demonstrated in the application that, in contrast to previous phase-contrast imaging configurations, a point source may be utilised, and moreover that the source may be broadly polychromatic provided its radiation has high lateral spatial coherence, which in practical terms indicates a maximum source diameter (s) dependent upon the source to object distance ($R_1$). The larger the source-object distance or the smaller the source size, the greater the lateral spatial coherence (see Wilkins et al *Nature* 384 335–8 (1996). A consequence of these disclosures in WO 96/31098 is that the approach proposed is more closely related to traditional methods used for absorption-contrast radiography and should be easier to implement than earlier proposals. This method of phase-contrast imaging is especially advantageous in the hard x-ray region where the lack of suitable lens elements make other techniques conventionally used in visible light and soft x-ray microscopy unsuitable.

It is an object of the present invention, at least in one or more embodiments, to provide a method of obtaining a phase-contrast image from a two-dimensional intensity record where the penetrating radiation substantially emanates from a point-like source. In one or more embodiments, it is a particular objective to provide a method adaptable to the extraction of phase and absorption-contrast information from radiographic images recorded with a microfocus source which need not be highly monochromatic.

SUMMARY OF THE INVENTION

In certain aspects, the invention involves the concept of obtaining two or more intensity records at a common finite distance after the radiation has emerged from the object, for respective different energy distributions of the radiation.

In one or more other aspects, the invention entails an appreciation that, with certain features, a point-like source configuration also lends itself to an approach based on the solution of a differential transport-of-intensity equation, albeit a different one from that used by others for the plane-wave case.

The invention is especially useful for separating out and retrieving phase information from a typical intensity record (obtained with a microfocus radiation source) which has both phase-contrast and absorption-contrast content.

In a first aspect, the invention provides method of obtaining an image of the phase change introduced by an object in penetrating radiation incident on the object, including:

irradiating the object with penetrating radiation having high lateral spatial coherence;

receiving at least a portion of said radiation at detector means after the radiation has emerged from the object and thereby obtaining and storing at least two intensity records for the received radiation each including intensity values at predetermined intervals; and utilising these values to derive a grid of values defining an image of the phase change introduced by the object in the penetrating radiation:

wherein said intensity records are obtained at a uniform finite distance after the radiation has emerged from the object, and are for respective different energy distributions of the detected radiation.

In its first aspect, the invention further provides apparatus for obtaining an image of the phase change introduced by an object in penetrating radiation incident on the object, including:

means to provide a source for irradiating an object with penetrating radiation having high lateral spatial coherence; and detector means for receiving at least a portion of said radiation after the radiation has emerged from the object whereby to generate at least two intensity records for the received radiation each including intensity values at predetermined intervals;

wherein said detector means is arranged for obtaining said intensity records at a uniform finite distance after the radiation has emerged from the object, and energy charactersing means is provided whereby said intensity records are for respective different energy distributions of the detected radiation.

In one embodiment, the respective different energy distributions are obtained by altering the energy spectrum of the radiation irradiating the object. This might be achieved, for example, by modifying the output of the radiation source, or by pre-filter means. In another embodiment, the respective different energy distributions are obtained by providing for the detector means to provide intensity as a function of energy in a certain energy band or band(s). For this purpose, a two-dimensional detector means may be variably wavelength sensitive, or be preceded by a variable filter shutter means. Further alternatively, the image intensity may be recorded as a function of photon energy for each pixel over a number of ranges of x-ray energy. Advantageously, for enhanced resolution, multiple intensity records may be obtained for respective multiple energy distributions of the radiation.

In the simplest case, each energy distribution may be a particular wavelength or photon energy level.

The aforesaid derivation may include solving one or more differential transport-of-intensity equations relating the phase at a plane of the object to the evolution of the intensity distribution along the direction of propagation, utilising predetermined uniform boundary conditions. An alternative derivation includes solving Fourier-optics equations. Others are of course possible for particular configurations or circumstances.

Preferably, the intensity values also reflect absorption contrast in the object, and the method further includes utilising these values to derive a grid of values defining an effective pure absorption-contrast image of the object.

With the apparatus of the first aspect of the invention, there is preferably further included a computer program product having a set of machine readable instructions which, when installed in a computer having a suitable operating system and memory means, configures the computer to be operable to utilise said values to derive a grid of values defining an image of the phase change introduced by the object in the penetrating radiation.

In a second aspect, the invention provides a method of obtaining an image of the phase change introduced by an object in penetrating radiation incident on the object, from one or more two-dimensional intensity records of penetrating radiation after it has traversed the object, the radiation being of high lateral spatial coherence when incident on the object and the or each record being obtained at a finite distance after the radiation has emerged from the object incorporating phase-perturbed components within a surrounding field of radiation either uniformly phase-perturbed or not phase-perturbed the method including:

storing intensity values from the or each record, at pre-determined intervals:

utilising these values and any predetermined uniform boundary conditions to derive a grid of values defining an image of the phase change introduced by the object in the penetrating radiation, by solving a differential transport-of-intensity equation relating the phase at an exit plane at the object to the evolution of the intensity distribution along the direction of propagation.

The invention also provides, in its second aspect, a method of obtaining an image of the phase change introduced by an object in penetrating radiation incident on the object, including:

irradiating the object with penetrating radiation having high lateral spatial coherence;

receiving at least a portion of the said radiation at a detector at one or more finite distances after the radiation has emerged from the object incorporating phase-perturbed components within a surrounding field of radiation either uniformly phase-perturbed or not phase-perturbed, and thereby obtaining and storing intensity values for the received radiation at predetermined intervals; and utilising these values and any predetermined uniform boundary conditions to derive a grid of values defining an image of the phase change introduced by the object in the penetrating radiation, by solving a differential transport-of-intensity equation relating the phase at an exit plane at the object to the evolution of the intensity distribution along the direction of propagation.

Preferably, the same intensity values are further utilised to also derive values defining an effective pure absorption-contrast image for the object.

The invention further provides, in its second aspect, an apparatus for obtaining an image of the phase change introduced by an object in penetrating radiation incident on the object, from one or more two-dimensional intensity records of penetrating radiation after it has traversed the object, the radiation being of high lateral spatial coherence when incident on the object and the or each record being obtained at a finite distance after the radiation has emerged from the object incorporating phase-perturbed components within a surrounding field of radiation either uniformly phase-perturbed or not phase-perturbed, the apparatus including:

(a) means for storing intensity values from the or each record, at pre-determined intervals; and (b) means, preferably including a stored program of machine readable instructions, for utilising said values and any predetermined uniform boundary conditions to derive a grid of values defining an image of the phase change introduced by the object in the penetrating radiation a phase-contrast image for the object, by solving a differential transport-of-intensity equation relating the phase at a plane at the object, e.g. an exit plane, to the evolution of the intensity distribution along the direction of propagation.

The invention also provides a set of machine readable instructions which, when installed in computer means also having suitable operating system software and memory means, configures the computer means for operation as apparatus according to the preceding paragraph. The invention still further provides a storage medium, e.g. a magnetic disk, a CD-ROM or optical storage disk, or an internet server, in which is stored said set of machine readable instructions.

The invention still further provides in its second aspect, apparatus for obtaining an image of the phase change introduced by an object in penetrating radiation incident on the object, including:

a source for irradiating an object with penetrating radiation having high lateral spatial coherence;

a detector for receiving at least a portion of said radiation a finite distance after the radiation has emerged from the object incorporating phase-perturbed components within a surrounding field of radiation not phase-perturbed or uniformly phase-perturbed, whereby to generate intensity values for the received radiation at pre-determined intervals; and computer means, including a stored program of machine readable instructions, operable to utilise said values and any predetermined uniform boundary conditions to derive a grid of values defining an image of the phase change introduced by the object in the penetrating radiation, by solving a differential transport-of-intensity equation relating the phase at an exit plane at the object to the evolution of the intensity distribution along the direction of propagation.

Preferably, the computer means is further operable to utilise the same intensity values to also derive values defining an effective pure absorption-contrast image for the object.

In one embodiment of the method of the second aspect of the invention, two of the intensity records obtained at different distances after the radiation has emerged from the object, e.g. in two distinct image planes. In another embodiment two or more of the intensity records are obtained at a uniform distance, e.g. in a single image plane, for different energy distributions of the incident radiation on the object. In a particular form of the latter embodiment, one or more of said intensity records are recorded such that image intensity as a function of photon energy is recorded for each pixel over a number of ranges of x-ray energy.

The transport-of-intensity equation relevant to the point source case may be equation (16), or in an alternative form, equation (18), hereunder, and the solution may be by a perturbation method. Alternatively, the equation may be solved numerically, especially when the last two terms of equation (16) have similar magnitudes.

As employed herein, the term "penetrating radiating" includes x-rays and neutrons, although the invention is especially useful for x-ray radiation, and may be substantially monochromatic but is more typically broadly polychromatic. An application of particular interest is the range 0.5 keV to 1 MeV, e.g. the hard x-ray range 1 keV to 1 MeV. The phase perturbation by the object may be thought of as a refraction effect or may more rigorously be viewed as a Fresnel diffraction effect. For an object of finite thickness within a surrounding medium, e.g. of different refractive index, the phase perturbation will also be dependent on the thickness of the object in the direction of the localised wave vector.

The object may, e.g., be a boundary, typically a boundary exhibiting a sharp variation in refractive index with respect to the penetrating radiation. The invention is especially useful where there is weak or negligible absorption contrast for the radiation between the intensities of the radiation passing through respective sides of the boundary, but may generally also be applied where there is significant absorption contrast at the boundary.

The boundary conditions typically do not need to be measured and may, e.g., include uniform Dirichlet, Neumann or periodic boundary conditions. The boundary conditions are selected to achieve a unique solution of the equation for phase, at least up to an arbitrary constant component.

Preferably, the solution further utilises one or more optical conditions. Such conditions may include e.g. a small wavefront curvature for the incident radiation, absence of focal points between the object and image, and uniform illumination of the object.

The incident penetrating radiation is not restricted to being monochromatic. For polychromatic radiation, the equation includes a spectrally weighted term or factor dependent on the square of the respective wavelength components.

BRIEF DESCRIPTION OF THE FIGURES

The invention will now be further described, by way of example only with reference to the accompanying figures in which.

PREFERRED EMBODIMENTS

Figure 1:
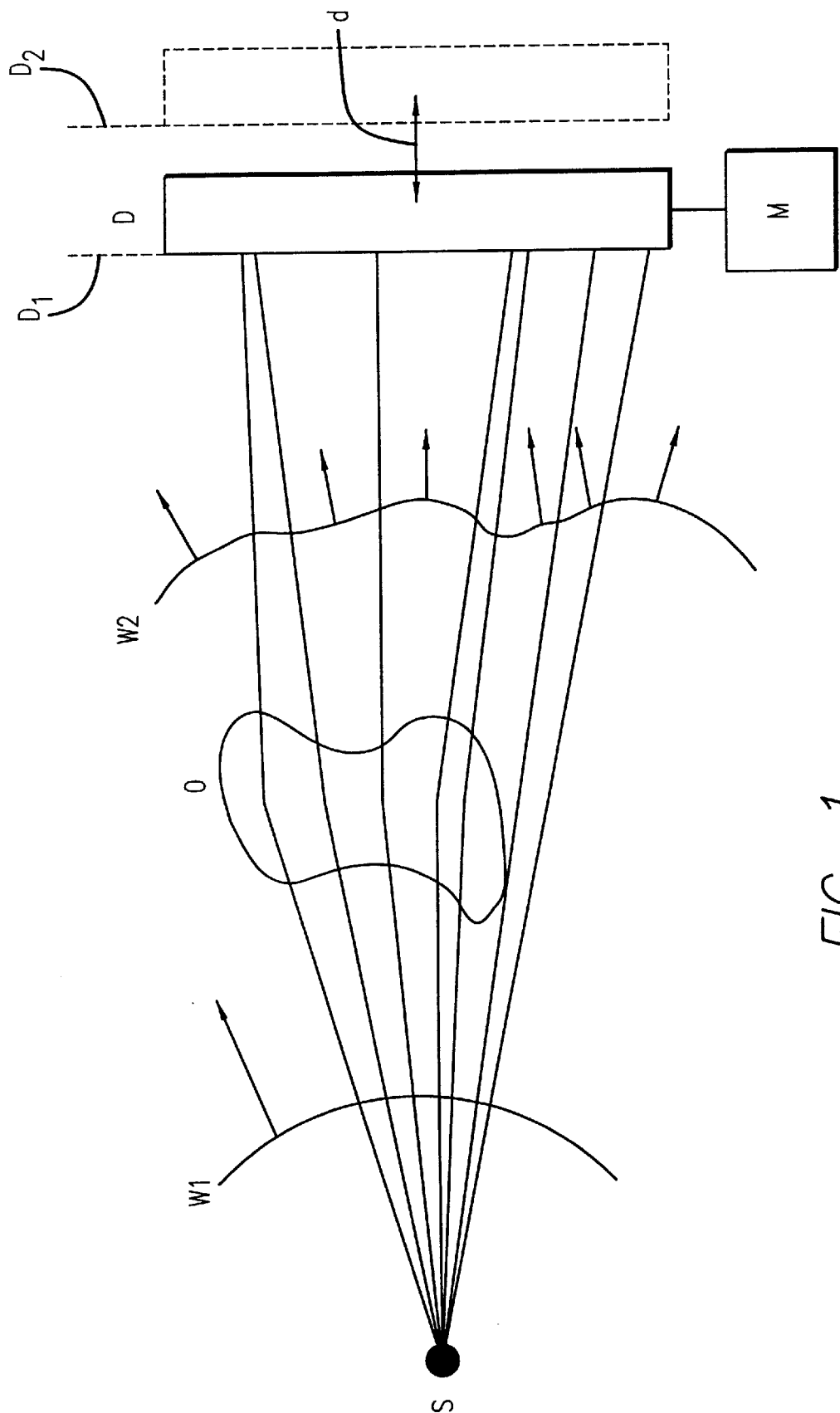
FIG. 1 is a diagram of an x-ray optics configuration according to an embodiment of the invention in which two intensity records are made at different detection planes.

The configuration illustrated in FIG. 1 includes a microfocus source S of high lateral spatial coherence and an x-ray two-dimensional imaging detector D, for example film, photostimulable phosphor plates (eg. Fuji image plates), or a two-dimensional electronic detector such as a charge-coupled device (CCD) array.

The term "lateral spatial coherence" herein refers to the correlation of the complex amplitudes of waves between different points transverse to the direction of propagation of the waves. Lateral spatial coherence is said to occur when each point on a wavefront has a direction of propagation which does not change over time. In practice, high lateral spatial coherence may, for example, be achieved by using a source of small effective size or by observing the beam at a large distance from the source. Generally, lateral coherence length $d\perp = \lambda R_1/s$, where $\lambda$ is the x-ray wavelength, $R_1$ is the source to object distance, and s is the maximum source diameter. For example for 20 keV x-rays and a source to object distance of 200 mm. a source size of approximately 20 $\mu$m diameter or less would typically be appropriate. The smaller the source size the better for the purposes of this invention, provided total flux from the source is sufficient. Lateral spatial coherence may need to be preserved by careful selection of the x-ray window of the source, e.g. such that it is of highly uniform thickness and homogeneity. The effects of partial spatial and temporal coherence on image contrast and resolution are described in Pogany et al [*Rev. Sci. Instrum.* 68 2774–82 (1997)].

Regions of refractive index variation transverse to the local direction of propagation, or thickness or density variations in the direction of propagation, can lead to a significant change in the local direction of propagation of the wave front passing through those regions.

Thus, referring again FIG. 1 a spherical wavefront W1 emanating from the point source S becomes distorted to W2 on passing through the object O. By recording the intensity of the wavefront at a sufficient distance from the sample, intensity variations due to rapid refractive index and thickness or density variations in the sample may be detected and their location recorded in an image. This corresponds to a form of differential phase-contrast imaging. The location of the imaging detector is chosen such that the spatial resolution of the detector is sufficient to resolve the intensity differences arising from the severe distortions of the wavefront and to optimise contrast subject to practical considerations. The values recorded at the detector also reflect absorption in the object and so the intensity values recorded at the detector also contain extractable absorption-contrast information.

For reasons to be explained subsequently, it is noted here that the object is disposed so that radiation which emerges from the object incorporates phase-perturbed components within a surrounding field of radiation not phase-perturbed or uniformly phase-perturbed.

Typically, the sharp gradients in refractive index or thickness will be imaged as sharp losses or rapid variations in intensity at corresponding points in the image. This feature of intensity loss or rapid variation at a given point in the image is to a first approximation essentially independent of wavelength and can therefore lead to very sharp contrast variations in the image even when a polychromatic source is used.

This configuration has the feature that for a circular source distribution, the spatial resolution in the image is the same for all directions and is essentially determined by the source size. It also has the advantage that considerable magnification of the image is possible and so recording media such as photostimulable phosphor image plates may be used which have many desirable properties such as wide dynamic range and high sensitivity but not high spatial resolution.

Detector D is typically coupled to suitable computing means M such as a personal computer utilising a 486 CPU, operating at 66 Mhz. and provided with appropriate memory and applications software.

Computer means M stores in memory a set of intensity values from the intensity record at detector D, at predetermined intervals in two-dimensions. In this simple case, the detector is a flat planar detector and the intervals are on a uniform square grid. The manner in which these values are derived will depend upon the kind of detector; for example, the detector may be of a pixellated structure in which each pixel is sampled in a two-dimensional scan and the values fed serially to the computer memory. Alternatively, the record may be made and stored in the detector and scanned or sampled as required by the computer.

Computer M further includes a control program by which the stored intensity values from the detector record and any predetermined uniform boundary conditions are utilised to derive a further grid of values defining an effective phase-contrast image in a selected plane of the object, by solving a differential transport-of-intensity equation.

For simplicity of formal development, we now discuss the theoretical aspects for the case of a monochromatic point source, with a view to defining a simple differential equation, and solution, applicable to a weak phase object, as described by conditions (4)–(6). The case of a broadly polychromatic source will be considered subsequently.

Figure 2:
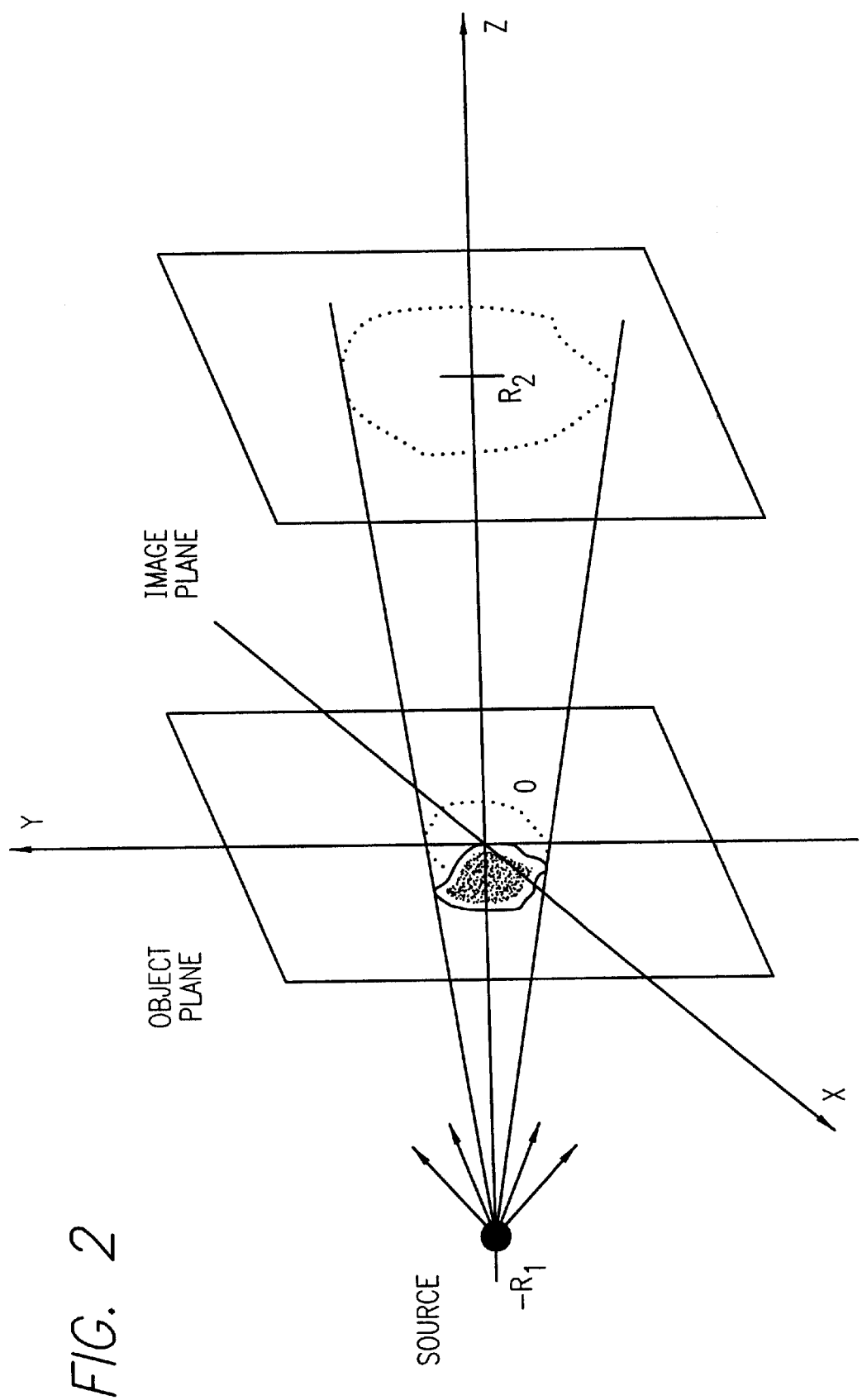
FIG. 2 is a diagram of a related co-ordinate system for the mathematical discussion which follows.

With reference to the co-ordinate system indicated in FIG. 2, consider a monochromatic point source with wavelength $\lambda=2\pi/k$ located at point $z=-R_1$, $R_1 >> \lambda$, on the optical axis Z. The source illuminates an object which is located between the source and the plane (x, y, 0) orthogonal to the optical axis at point z=0, the object being bounded on the right hand side by the plane z=0 (FIG. 2). The object is assumed to be thin, i.e. its z-dimension is much smaller than $R_1$.

Let $$u_0(x, y) = \frac{\exp(ik\sqrt{x^2 + y^2 + R_1^2})}{\sqrt{1 + (x^2 + y^2)/R_1^2}} a(x, y)\exp\{ik\psi(x, y)\} \quad (1)$$

be the scalar complex amplitude at the object plane z=0, where $\phi(x,y)=k\psi(x,y)$ is the phase "aberration" appearing due to the transmission of the wave through the object and $I(x,y)=a^2(x,y)$ is the corresponding intensity.

The propagation of the amplitude $u(x,y,0)=u_o(x,y)$ into the source-free half-space z>0 is governed by the Helmholtz equation $$(\nabla^2 + k^2)u = 0. \quad (2)$$

A solution to the Helmholtz equation, such that $u(x,y,0)=u_o(x,y)$, is given by the first Rayleigh-Sommerfield integral. This integral can be written for $z>>\lambda$ as $$u(x', y', z) \cong -\frac{ik}{2\pi} \int\int \frac{\exp(ikr)}{r} \frac{z}{r} u_0(x, y)dxdy, \quad (3)$$

where $r=\sqrt{(x'-x)^2+(y'-y)^2+z^2}$.

In order to simply the analysis, we assume that our object is small compared to its distance from the source and is weakly scattering, i.e.

$$\psi(x,y)\equiv 0 \text{ and } \alpha(x,y)\equiv 1, \text{ when } (x^2+y^2)\geq d^2 \cdot d << R_1; \quad (4)$$

$$|\partial^m_x \partial^n_y \psi(x,y)| << (R')^{1-n+m}, m^2+n^2>0. \quad (5)$$

$$|\alpha(x,y)|\geq C>0 \text{ and } |\partial^m_y \alpha(x,y)| << Ck|\partial^m_x \partial^n_y \psi(x,y)|, m^2+n^2>9 \quad (6)$$

where $R'=R_1R_2/(R_1+R_2)$ and $z=R_2$ is the position of the "image" plane, $R_2>>\lambda$.

Condition (4) requires the wavefront incident on the object to have a small curvature. Condition (5) also has a simple physical meaning: it ensure, in particular that there are no focal points between the object plane z=0 and the image plane $z=R_2$ (as $|\nabla^3\psi|<<1/R'$). In the absence of condition (5) phase distribution in the image plane may relate to intensity distribution in the object plane in a more complex manner due to possible focal phase shifts. Condition (6) essentially requires the incident beam to illuminate the object uniformly and the variations of the imaginary part of the refractive index inside the object to be much weaker than the variations of its real part at a given x-ray wavelength $\lambda$. The last requirement applies both for "phase" objects, and also for mixed phase/absorption objects.

Conditions (4 to 6) guarantee that the diffraction angles are small. Therefore, under these conditions the image can be calculated using the Fresnel integral:

$$u(x', y', R_2) = -\frac{ik}{2\pi}\frac{\exp(ikR)}{R_2}\int\int \exp\{ikS(x, y)\}a(x, y)dxdy, \quad (7)$$

where $R=R_1+R_2$ and $$S(x, y) = \frac{(x'-x)^2 + (y'-y)^2}{2R_2} + \frac{x^2+y^2}{2R_1} + \psi(x, y). \quad (8)$$

Applying the stationary phase formula to integral (7) we obtain:

$$u(x', y', R_2) = \sum \frac{\exp\{i[kR + kS(x_s, y_s) + (\pi/2)\mathrm{sgn}S_s'']\}}{R_2\sqrt{\det S_s''}} a(x_s, y_s) + O(k^{-1}), \quad (9)$$

where the sum is over all stationary points (x,y,) corresponding to image (x', y'), sgn S", is the number of negative eigenvalues of the matrix S" of second-order partial derivatives of the phase function S evaluated at point (x, y,) and det S", is its determinant, $|O(k^{-1})| \leq \mathrm{const}/k$. Conditions (6) ensure that the residual term $O(k^{-1})$ is much smaller than the leading terms in (9).

Calculating partial derivatives of the phase function (8) and equating them to zero, we obtain the following equations for the stationary points $(x_1 y_1)$:

$$x' = Mx_1 + R_3\psi_x(x_1, y_1)$$
$$y' = My_1 + R_2\psi_y(x_1, y_1) \quad (10)$$

where $M = (R_1 + R_1)/R_1$
and where we used notation of the type $\psi_y'$ for partial derivatives: $\psi_u' = \partial\psi/\partial_y$. Equations (10) describe ray trajectories originating on the object plane at points $(x_1, y_1)$ and ending up at a given point $(x', y', R_2)$ of the image; constant M is the coefficient of image magnification. Condition (5) ensures that equations (10) have only one solution, $(x_1, y_1)$, i.e. there is only one ray connecting each point of the image with the corresponding unique point of the object. Consequently, the summation sign in (10) can be omitted.

It is straightforward to calculate the matrix of second-order partial derivatives of the phase function:

$$S''(x, y) = \begin{pmatrix} (1/R') + \psi_{xx}'' & \psi_{xy}'' \\ \psi_{xy}'' & (1/R') + \psi_{yy}'' \end{pmatrix}. \quad (11)$$

This matrix describes the variation of the curvature of the wavefront. In view of condition (5) this matrix is non-degenerate, both its eigenvalues are positive (hence, sgn S"=0) and its determinant can be approximated by $$\det S'' = (1 + R'\nabla^2\psi)/R'^2, \quad R'|\nabla^2\psi| \ll 1. \quad (12)$$

Now we can simplify the stationary phase formula (9):

$$u(x', y', R_2) \cong \frac{a(x_s, y_s)}{M\sqrt{1 + R'\nabla^2\psi}} \exp\{iS(x_s, y_s)\}. \quad (13)$$

The corresponding intensity distribution on the image plane is $$I(x', y', R_2) \cong M^2 I(x_1, y_1)[1 - R'\nabla^2\psi(x_1, y_1)]. \quad (14)$$

Let us now use the stationary-point equations (10) to further simplify equation (14):

$$I(x_s, y_s) = I(M^{-1}x' - M^{-1}R_2\psi_x, M^{-1}y' - M^{-1}R_3\psi_y) \quad (15)$$
$$\cong I(M^{-1}x', M^{-1}y') - R'(\nabla I \cdot \nabla \psi)(M^{-1}x', M^{-1}y').$$

Substituting (15) into (14) and denoting $x = M^{-1}x'$, $y = M^{-1}y'$, we obtain $$M^2 I(Mx, My, R_2) \cong I(x,y)[1 - R'\nabla^2\psi(x,y) - R'\nabla \log I(x,y) \cdot \nabla\psi(x,y)] \quad (16)$$

This equation describes the image of a weak phase object (as described by conditions (4)–(6)) as a function of the source-to-object and object-to-image distances. It shows that in the case of negligible absorption the image contrast is proportional to "focal" distance R' and to the Laplacian of the phase shifts introduced into the incident beam on passing through the object. Note that formula (16) in the case of $\nabla\psi = 0$ and $\nabla^2\psi = 0$ trivially gives the exact value of intensity in the absence of any objects between the source and the image plane.

For x-ray wavelengths away from absorption edges of the material of the object, the linear attenuation coefficient $\mu$ is known to be approximately proportional to $\lambda^2$ and $$\psi(x, y) = \frac{\lambda^2 r_s}{2\pi} \int_{-\infty}^{0} \rho(x, y, z) dz, \quad (17)$$

where r is the classical electron radius and $\rho$ is the electron density of the object. These facts and equation (16) imply that in the accepted approximation the image contrast has a simple quadratic dependence on the wavelength. Therefore, polychromaticity of the source is not necessarily an obstacle to the application of this method and can be explicitly taken into account: the factor $\lambda^2$ is then replaced by a spectrally weighted sum dependent on the square of the respective wavelength components.

Equation (16) can be used for explicit retrieval of the phase from intensity measurements in two image planes, indicated at $D_1$ and $D_2$ in FIG. 1. To see how this may be achieved, it is convenient to rewrite the equation in the following form:

$$-\nabla[I(x,y)\nabla\psi(x,y)] = F(x,y), \quad (18)$$

where $F(x,y) = [M^2 I(Mx, My, R_2) - I(x,y)]/R'$. Equation (18) relates the transverse derivatives of the phase on the object plane to the intensity distributions on the object and image planes.

Equation (18) is similar to the plane-wave transport-of-intensity equation (TIE) which can be formally obtained from (18) when $R_2 \to 0$. There are, however, some important differences. First, unlike the TIE, equation (18) does not assume the distance between the two planes $D_1$, $D_2$ where intensity is measured, to be infinitesimally small. Second, equation (18) takes image magnification explicitly into account, and, therefore, is more appropriate for phase imaging with a point source. It can be readily seen that an attempt to directly apply the plane-wave TIE to imaging with a spherical incident wave leads to a different function on the right-hand side of equation (18), namely the distance R' in the denominator of F(x,y) is replaced by $R_2$. The resulting error is due to the extra wavefront curvature produced by the incident spherical wave and is negligible only when $R_2 \ll R_1$. Finally, our method of derivation of equation (18), which was based on the application of the stationary phase formula to the Fresnel integral, allowed us to formulate the validity conditions (4)–(6) in terms of the amplitude distribution $u_0(x,y)$ on the object plane. These are effectively conditions on the optical properties of the source, the sample and the geometrical parameters of the imaging layout. In contrast to this, the conventional method for deriving the plane-wave TIE from the Hemholtz equation involves requirements on the diffracted amplitude u(x,y,z), z>0, which are difficult to verify in practice.

In order to find a unique solution to (18) one needs to define some boundary conditions for it. Such boundary conditions can be readily obtained using condition (4). If Ω is a simply connected domain in the plane (x,y,0) containing the circle of radius d with the centre at the origin of coordinates, then on the boundary Γ of Ω we have $$\psi(x,y)|_\Gamma = 0. \tag{19}$$

In fact, one can define not only the Dirichlet boundary conditions (19), but any uniform boundary conditions on Γ, e.g. the Neumann or the periodic ones. This situation is very different from that encountered in astronomical adaptive optics, where the plane-wave TIE is also used for phase retrieval. There the distorted wavefront is not surrounded by the primary unperturbed or uniformly perturbed one as in the present situation and, therefore, boundary conditions must always be measured directly.

In the case where the primary unperturbed or uniformly perturbed wavefront is not measured, a procedure of artificially blurring the image at the edges of the image field or of iteratively retrieving the phase and recalculating the intensity distribution in the region around the edges of the object to effectively create uniform boundary conditions might be used.

Equation (18) with boundary conditions (19) has a unique solution for phase, provided $I(x,y) \geq C^2 > 0$ in Ω, where C is a constant defined in (6), while solutions to similar problems with the Neumann and periodic boundary conditions are unique up to an arbitrary additive constant. The requirement for the intensity to be non-zero is satisfied due to conditions (6).

Solutions to the problem (18)–(19) and similar problems with the Neumann and periodic boundary conditions are stable with respect to errors in the right-hand side function F(x,y). Note, however, that errors in $M^2 I(Mx, My, R_2)$ and I(x,y) should preferably be small compared not only to these intensities, but to their difference which has to be much smaller than the intensities themselves according to equation (16) and condition (5). Therefore, it is preferred, strongly, that the measured intensity data be fairly "clean" from noise to optimise the reliability of quantitative retrieval of the phase.

In the case of uniform intensity, $I(x,y) = I_0$ on the object plane a simple solution to equation (18) with the periodic boundary conditions in the square $(-D,D) \times (-D,D)$. D>d, can be given by the formula $$\psi_{mn} = \left(\frac{D}{\pi}\right)^2 \frac{\tilde{F}_{mn}}{(m^2+n^2)}, \quad m^2 + n^2 > 0. \tag{20}$$

where $\psi_{mn}$ and $\tilde{F}_{mn}$ are the Fourier coefficients of $\psi(x,y)$ and the (experimentally measurable) function $\tilde{F}(x,y) = [M^2 I(Mx, My, R_2) - I_0]/(I_0 R')$, respectively.

In the general case of non-uniform intensity distribution on the object plane, the last two terms in equation (16) can be comparable in magnitude. However, in many real situations, where the illuminating wave has uniform intensity and absorption in the object is moderate, but not negligible, the last term in equation (16) may be smaller than the rest. In such cases equation (18) can be solved by perturbation methods. In particular, it is easy to show that an equation to (20), but with the constant intensity $I_0$ in the numerator of the function $\tilde{F}(x,y)$ replaced by the measured variable intensity distribution I(x,y), can be considered as a first order approximation to the exact solution of equation (18).

Finally, when the last term in equation (16) has a similar magnitude to the preceding one, system (18)–(19) can be solved numerically using one of the well known methods for the Laplace equation on the plane.

It is believed that the described derivation and radiographic method and apparatus provide a practical technique for deriving phase-contrast information contained in one or more detected intensity distributions in two dimensions. The configuration shown in FIG. 1 is straight forward and akin to configurations traditionally used for absorption-contrast radiography. The disclosed method for deriving the phase-contrast image is particularly suited to planar detectors of a pixellated or grid construction or which are read in an incremental manner, and all the more suitable to the combination of such detectors and digital computers.

Furthermore, by processing the detector values for absorption-contrast by conventional methods, one can simultaneously derive both phase-contrast and absorption-contrast images from, say, radiographic recordings in two or more two-dimensional planes $D_1$, $D_2$.

Recording of two image intensity distributions at different distances $D_1$, $D_2$ in order to carry out phase retrieval may not always be convenient or practical. For example, the measurement of intensity in two planes at different positions along the optic axis usually requires precision movements of the detector system D (indicated by arrow d in FIG. 1) which may be undesirable in real-life applications. A second method of phase retrieval in the present approach may be achieved by measuring two or more intensity distributions in an image plane at fixed distance from the object but with two or more distinct distributions of incident energy, e.g. different wavelengths in a simple case or even more advantageously by using a 2-dimensional energy-sensitive detector such as those based on Cd—Mn—Te. With reference again to FIG. 2, consider a paraxial wavefield in the free half-space $z \geq 0$ in an arbitrary state of temporal and spatial coherence with complex amplitude.

$$U(r,t) = \int U(r,v) \exp(i 2\pi v t) dv, \tag{21}$$

where $v = ck/(2\pi)$ is the frequency, k is the wavenumber and c is the speed of light in vacuum. Let S(r,v) be the (power) spectral density, then $$S(r_\perp, R, v) - S(r_\perp, v) = -R \nabla_\perp \bullet [S(r_\perp, v) \nabla_\perp \psi(r_\perp, v)], \tag{22}$$

where $k\psi(r_\perp, v) = \arg U(r_\perp, v)$ and we omit z=0 from the list of arguments of all functions. In the monochromatic case we have $U(r,v) = U(r)\delta(v-v_0)$, $S(r,v) = I(r)\delta(v-v_0)$ and the phase $k\psi(r,v_0)$ coincides with $k\psi(r_\perp) = \arg U(r_\perp)$.

The TIE can be obtained by integrating equation (22) over the frequency range:

$$I(r_\perp, R) - I(r_\perp) = -R \nabla_\perp \bullet [\int S(r_\perp, v) \nabla_\perp \psi(r_\nabla, v) dv], \tag{23}$$

where $I(r) = \int S(r,v) dv$ is the (time-average intensity [14]. As already discussed, this form of the TIE relates the difference between the intensity distributions in the object and the image planes to the phase derivatives in the object plane.

If spatial variations of the spectral density are much weaker than the corresponding phase variations, then equation (22) can be simplified:

$$S(r_{195}, R, v) = S(r_\perp, v)[I - R \nabla_\perp^2 \psi(r_\perp, v)]. \tag{24}$$

This situation is typical for phase objects, i.e. objects with the real part of the refractive index varying much stronger than its imaginary part at the given wavelength. This is the case e.g. for thin biological samples imaged with high-energy x-rays. For such objects conventional images based on absorption often have poor contrast, while phase-contrast images are much more informative [5, 8, 9].

Let us assume that the propagation of x-rays through the sample is paraxial and rectilinear. Then the spectral density and the phase in the object plane can be expressed as $$S(r_\perp, v) = S^{in}(r_\perp, v) \exp\{-\int \mu(r_\perp, z', v) dz'\}, \quad (25)$$

$$\psi(r_\perp, v) = \psi^{in}(r_\perp, v) - \int \delta(r_\perp, z', v) dz', \quad (26)$$

where the values with superscript "in" correspond to the wave incident on the sample, integration is through the sample along the lines parallel to the optic axis, 1-δ is the real part of the refractive index and $\mu$ is the linear absorption coefficient. If all wavelengths present in the spectrum are sufficiently far away from the absorption edges of the sample material, then $$\mu(r,v) \equiv \sigma^3 \mu(r,v_0), \quad (27)$$

$$\delta(r,v) \equiv \sigma^2 \delta(r,v_0). \quad (28)$$

where $\sigma = v_0/v$ and $v_0$ is some fixed frequency from the spectrum. Substituting equations (25)–(28) into equation (24), we obtain $$S(R,v) = S^{in}(v) \exp(-\sigma^3 M_0)[1 - R\nabla_\perp^2 \psi^{in}(v) + R\sigma^2 \nabla_\perp^2 \psi_0], \quad (29)$$

where we omitted $r_\perp$ from the list of arguments of all functions and denoted $M_0 = \int \mu(r_\perp, z', v_0) dz'$ and $\psi_0 = \int \delta(r_\perp, z', v_0) dz'$. The last two terms in the square brackets in equation (29) must be much less than one if for example the paraxial approximation is valid.

If the characteristics of the radiation incident on the sample, i.e. $S^{in}(v)$ and $\psi^{in}(v)$, are known, and the spectral density at a given frequency at the image plane, $S(R,v)$, can be measured (e.g. with the help of an energy-sensitive detector), then equation (29) can be used for phase retrieval from two such measurements at different wavelengths. Indeed, if, for example, $S(R,v)$ and $S(R,v_0)$ have been measured, then writing e.g. equation (29) for v and $v_0$ and excluding $\exp(-\sigma^3 M_0)$ from these equations, it is possible to derive $$-\nabla_\perp^2 \psi_0 = \frac{1 - \gamma - R[\nabla_\perp^2 \psi^{in}(v) - \gamma \sigma^3 \nabla_\perp^2 \psi^{in}(v_n)]}{R\sigma^2(1 - \gamma\sigma)}, \quad (30)$$

where $$\gamma = \frac{S(R, v)}{S^{in}(v)} \left[\frac{S^{in}(v_0)}{S(R, v_0)}\right]^{\sigma^3}. \quad (31)$$

The phase $\psi_0(r_\perp)$ can be recovered by solving the Poisson equation (30). Note that any uniform boundary conditions can be assigned to $\psi_0$, if the image is surrounded by the unperturbed primary beam. The solution to equation (30) with typical uniform boundary conditions is always unique at least up to an arbitrary additive constant. It is obvious from equations (30) and (31) that the stability of phase recovery is determined by the ratio $\sigma = v_0/v$ of the two frequencies and the ratio of the spectral densities in equation (31). In an experiment these values can be chosen to be sufficiently different from unit, in which case the recovery of the phase using equation (30) will be stable with respect to errors in the experimental data. Therefore, this technique may have an advantage over the earlier-described method of phase recovery from intensity distribution in the beam cross-sections at two different positions along the optic axis. Indeed, in this latter case the z-distance between the cross-sections must be small and the difference between the two intensity distributions has to be small too, so the calculation of the phase Laplacian is a numerically unstable procedure of the "division of zero by zero" type.

As with the earlier embodiments of the invention, an analog of equation (30) suitable for in-line phase imaging with a small polychromatic source can be derived. The additional curvature appearing in the wavefront due to the quasi-spherical nature of the incident beam can be explicitly taken into account. Consider the following "quasi-spherical" analog of equation (22):

$$M^2 S(Mr_\perp, R, v) - S(r_\perp, v) = -R'\nabla_\perp \bullet [S(r_\perp, v)\nabla_\perp \psi(r_\perp, v)]\}, \quad (32)$$

where $M = (R_1 + R)/R_1$ is the magnification coefficient. $R' = (R_1^{-1} + R^{-1})^{-1}$ and $R_1$ is the source-to-object distance. Starting from equation (32) and proceeding exactly as above, it is straightforward to derive the Poisson equation for the phase similar to equation (30), but with $\psi^{in}(r_\perp, v)$ replaced by $\psi'^{in}(r_\perp, v) = \psi^{in}(r_\perp, v) - r_\perp^3/(2R_1)$, R replaced by R' and $\gamma$ replaced by $$\gamma' = M^{2(1-\sigma^3)} \frac{S(Mr_\perp, R, v)}{S^{in}(r_\perp, v)} \left[\frac{S^{in}(r_\perp, v_0)}{S(Mr_\perp, R, v_0)}\right]^{\sigma^3}. \quad (33)$$

In a slightly different experimental arrangement without an energy-sensitive detector it may be possible to perform intensity measurements in the image plane with two different monochromatic incident beams with frequencies v and $v_0$. Then the above equations (30) and (32) still hold with the replacement of all spectral densities by the corresponding intensities.

It is now proposed to outline a method for phase retrieval from polychromatic images obtained using only a conventional (not energy-sensitive) detector. Let us assume that the transversal variations of absorption are so weak that $$\exp(-\sigma^3 M_0(r_\perp)) \equiv \exp\{-\sigma^3 \overline{M}_0\}[1 - \sigma^3 M'_0(r_\perp)], \quad (34)$$

where $\overline{M}_0$ is the "average" absorption in the sample at $v = v_0$, while $1\sigma^3 M'_0(r_\perp) 1 \ll 1$ everywhere. The constant $\overline{M}_0$ can be determined from the knowledge of total intensity incident on the sample and the total intensity of the image. The weak local variations $M'_0$ of absorption are assumed unknown.

In the first crude approximation one may choose to neglect the term $M'_0(r_\perp)$. Then the following Poisson equation for the phase can be easily derived from equation (29):

$$-\nabla_\perp^2 \psi_0 = \frac{I(R) - \int S^{out}(v)[1 - R\nabla_\perp^2 \psi^{in}(v)] dv}{R \int S^{out}(v) \sigma^2 dv}, \quad (35)$$

using the notation $S^{out}(v) = S^{in}(v) \exp\{-\sigma^3 \overline{M}_0\}$. Therefore, in this case the phase can be found from only one polychromatic image $I(R) \equiv I(r_\perp, R) = \int S(r_\perp, R, v) dv$ by solving equation (35), providing the properties of the incident radiation, i.e. $S^{in}(v)$ and $\psi^{in}(v)$, are known a priori.

It is now proposed to demonstrate that, if the weak local variations $M'_0(r_\perp)$ of absorption have to be taken into account, the phase can be found from two polychromatic images obtained with the incident beams having different spectral composition. Substituting equation (34) into equation (29) and integrating over the frequency range, we obtain $$a - bM'_0 - c\nabla_\perp^2 \psi_0 + dM'_0 \nabla_\perp^2 \psi_0 = 0. \quad (36)$$

where $a = I(R) - \int S^{out}(v)[1 - R\nabla_\perp^2 \psi^{in}(v)] dv$, $b = -\int S^{out}(v)[1 - \$\nabla_\perp^2 \psi^{in}(v)]\sigma^3 dv$, $c = R \int S^{out}(v) \sigma^2 dv$ and $d = -\int S^{out}(v)\sigma^5 dv$.

Given two images, $I_j(R)$, j=1.2, measured with incident beams having different spectral composition (described by the a priori known distributions $S_j^{in}(v)$ and $\Psi_j^{in}(v)$, j=1.2). $M_0'$ can be eliminated from the corresponding pair of equations (36) and obtain $$-\nabla_\perp^2 \psi_0 = \frac{a_1 b_2 - a_2 b_1}{b_1 c_2 - b_2 c_1 + a_2(d_1 - d_2 b_1/b_2)}, \tag{37}$$

with all quantities defined for each of the incident beams exactly as above, e.g. $\alpha_j = 1_j(R) - \int S_j^{out}(v)[1 - R\nabla_\perp^2 \Psi_j^{in}(v(]$ dv, j=1,2, etc. similarly, it is possible to solve for $M_0$ to obtain an effective pure absorption-contrast image.

These expressions have demonstrated that the x-ray phase can be recovered using the Transport of Intensity equation from polychromatic images obtained at a fixed position along the optic axes. It can be done with a quasi-plane or a quasi-spherical paraxial incident wave, whose spectral density and the phase of the monochromatic components are known a priori. The approach would preferably involve a substantially complete characterisation of the source prior to phase retrieval experiments. The above-described embodiments of the invention demonstrate that effective phase- and absorption-contrast images can be obtained, in a variety of ways including any one of the following:

(1) From two images obtained with monochromatic incident beams with two different wavelengths (photon energies).

(2) With a polychromatic incident beam and measurement of the image intensity as a function of x-ray energy using and energy-sensitive detector (e.g. based on cadmium manganese telluride), with some binning of the energy values to give sufficient image intensity in at least two energy ranges (bins).

(3) With a polychromatic incident beam and measurement of the image intensity using some energy selectivity in the detector, for example by the use of energy filters based on the use of absorber foils. In practice this might involve using a pair of x-ray films with an appropriate filter foil between them to simultaneously record suitable image intensity data.

(4) From two polychromatic images obtained with incident beams having different spectral composition and a conventional, rather than energy-sensitive, detector.

In each of these above situations, just one measurement of an image is sufficient for phase recovery if the transverse spatial variations of absorption are negligible. Otherwise, it is possible to obtain separate effective phase- and absorption-contrast images from the image intensity data.

Figure 3:
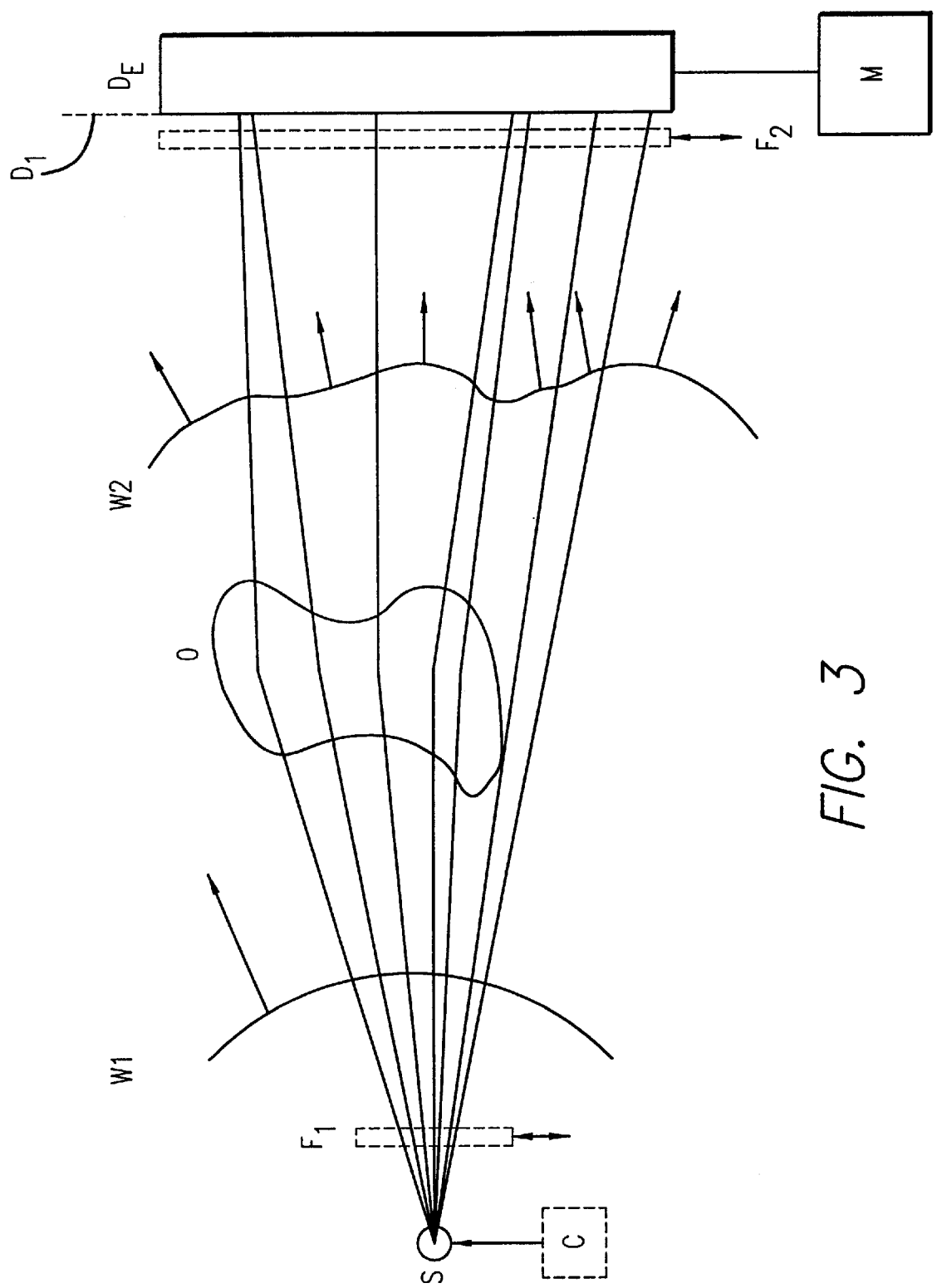
FIG. 3 is a diagram of an alternative x-ray optics configuration in which two intensity records are made at a common detection plane for respective different energy distributions of the radiation.
Figure 4:
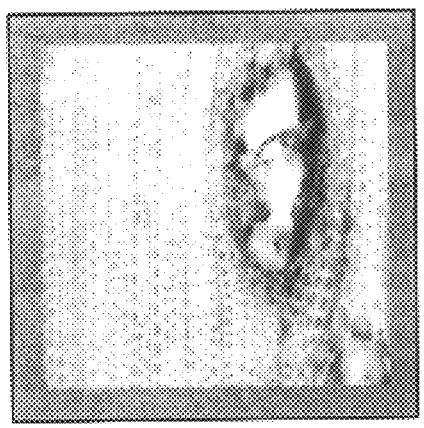
FIGS. 4 to 9 illustrate successive intensity records in a mathematical test case of a method utilising one approach to the invention.
Figure 5:
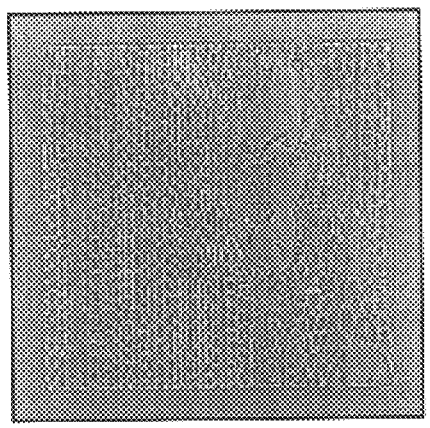

FIG 3 diagrammatically illustrates a variety of arrangements of deriving plural intensity records for respective different energy distributions. Such measurements can be performed, for example, with an energy-sensitive detector $D_E$, or with a source turnable by adjustable control C to vary its wavelength profile, or with a polychromatic source S and interchangeable monochromators or filters either ahead of the object ($F_1$) or after the object, e.g. as a shutter $F_2$ front of the non-energy sensitive CCD detector D. If absorption in the sample is negligible, the phase can be found from intensity of only one polychromatic image, provided the properties of the incident radiation are known a priori.

Other approaches to using two or more different spectral distributions (i.e. alternatives to approaches based on transport-of-intensity equations) may involve deconvolution of the spectral distribution from the data or, alternatively, a least squares-type fitting procedure to extract $\nabla^2 \Psi$. Even more sophisticated methods based on Bayesian analysis might also be used. It is proposed to now briefly outline phase and absorption retrieval by a technique based on a Fourier optics approach.

The treatment of phase retrieval in the spherical-wave case is analogous to the treatment for the plane-wave case and quite straightforward. This section is thus confined to the latter.

It may be shown that in the plane-wave case. Cowley's form of the Kirchhoff's formula for the x-ray wave function can, with certain small-angle approximations, be reduced to:

$$\psi(x,y) = \frac{i}{\lambda R_2} \psi_0(x,y) \exp\left(-ik\frac{x^2+y^2}{2R_2}\right) * q(x,y) \tag{38}$$

and therefore $$\Im[\psi(x,y)] = \psi(f_x,f_y) = \psi_0(x,y)\exp[i\pi\lambda R_2(f_x^2+f_y^2)]Q9f_x,f_y), \tag{39}$$

where we adopt the convention that real-space functions are in lower-case and the corresponding frequency-space functions (after taking Fourier transforms) are in upper-case, e.g. $Q(f_x,f_y) = \Im[q(x,y)]$. For a further discussion of the steps involved in this derivation, see J. M. Cowley (1975) *Diffraction Physics* )North-Holland : Amsterdam.). Relevant theoretical discussion is also to be found at Pogany et al (1997) Rev. Sci. Inst. 68, 2774–2782.

The transmission function can be written, assuming $\phi(x,y)t(x,y)$ and $\mu(x,y)t(x,y)$ are sufficiently small, as $q(x,y) = 1 + i\phi'(x,y) - \mu'(x,y)$, where $\phi'(x,y) = -\phi(x,y)t(x,y)$ and $\mu'(x,y) = \mu(x,y)t(x,y)/2$. The Fourier transform of the transmission function is then given by $Q(f_x,f_y) \approx \delta(f_x,F_y) + i\Phi'(f_x,f_y) - M'(f_x,f_y)$. Equation (39) can then be written as $$\psi(f_x,f_y) \approx \psi_0 \exp[i\chi(f_x,f_y) + i\Phi'(f_x,f_y) - M'(f_x,f_y)], \tag{40}$$

where $\chi(f_x,f_y) = \pi\lambda R_2(f_x^2 + f_y^2)$. By expanding (40) and taking inverse Fourier transforms of both sides, one can obtain, to first order in $\phi'$ and $\mu'$, and omitting the functional dependence:

$$I = 1 - 2\phi' * \Im^{-1}[\sin(\chi)] - 2\mu' * \Im^{-1}[\cos(\chi)]. \tag{41}$$

Consequently, in the case of a pure-phase object, one can retrieve the $\phi t$-distribution from a single image:

$$\phi t = \mathcal{F}^{-1}\left[\frac{\mathcal{F}(I-1)}{2\sin(\chi)}\right], \tag{42}$$

and, in the case of a pure-absorption object:

$$\mu t = -\mathcal{F}^{-1}\left[\frac{\mathcal{F}(I-1)}{\cos(\chi)}\right]. \tag{43}$$

In the more usual case of an object for which both phase and absorption effects are significant, two images, $I_1$ and $I_2$, which have been collected with different values of $R_2$ and/or x-ray energy (we are discussing the monochromatic case here, but in the polychromatic case two different voltage settings of the x-ray source, giving two different spectral distributions, would be appropriate) could be used. Assuming, in the absence of any absorption edges for constituent elements, that $\mu_2 = (\lambda_2/\lambda_1)^3 \mu_1$ and that $\phi_2 = (\lambda_2/\lambda_1)$ $\phi_1$, the resulting simultaneous equations can be solved to yield:

$$\phi t = -\mathcal{F}^{-1}\left[\frac{\mathcal{F}(I_2-1)\cos(\chi_1) - \left(\left[\frac{\lambda_2}{\lambda_1}\right]\right)^3 \mathcal{F}(I_1-1)\cos(\chi_2)}{2\left[\left(\left[\frac{\lambda_2}{\lambda_1}\right]\right)^3 \sin(\chi_1)\cos(\chi_2) - \left[\frac{\lambda_2}{\lambda_1}\right]\sin(\chi_2)\cos(\chi_1)\right]}\right] \quad (44)$$

and $$\mu t = \mathcal{F}^{-1}\left[\frac{\left[\frac{\lambda_2}{\lambda_1}\right]\mathcal{F}(I_1-1)\sin(\chi_2) - \mathcal{F}(I_2-1)\sin(\chi_1)}{\left[\frac{\lambda_2}{\lambda_1}\right]^3 \sin(\chi_1)\cos(\chi_2) - \left[\frac{\lambda_2}{\lambda_1}\right]\sin(\chi_2)\cos(\chi_1)}\right] \quad (45)$$

The advantages of using the multiple energy method of retrieving phase rather than the multiple distance method include the following:

- ability to record data by electronic rather than mechanical change of image conditions (for example by rapid switching of tube voltage or energy-sensitive detectors) leading to the possibility of very rapid phase retrieval; and
- ability to use 2-dimensional energy dispersive detectors (e.g. those based on CdMnTe) as these become available, in order to record a large number of 2-dimensional images for different x-ray energy ranges.

EXAMPLE 1

To test the validity of the method of the invention utilising transport-of-intensity equations, a numerical example was prepared with simulated date, and the successive steps are illustrated in FIGS. 4 to 9.

A perfectly monochromatic x-ray point source was assumed with wavelength $\lambda=0.154$ nm (CuK$_0$ radiation), and source-to-object and object-to-image distances $R_1=R_2=0.2$ m, so that $R'=0.1$ m and $M=2$ (FIG. 2). A pure phase object was also assumed, of size 640×640 $\mu$m$^2$, producing the phase distribution on the object plane (x,y,0) shown in FIG. 4. The range of the phase values was [−0.8667, 0.6706] radians.

Figure 6:
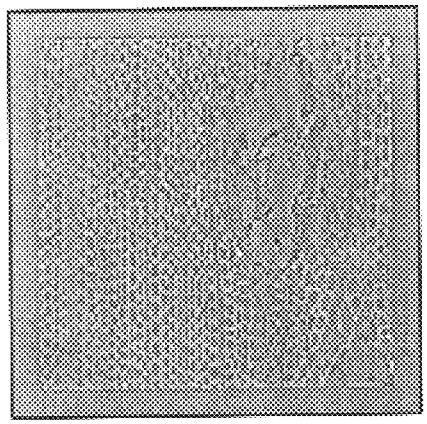

The intensity distribution $I(x,y,R_2)$ on the image plane was then calculated by computing the Fresnel integral (7 above) on a grid with 128×128 pixels. The scaled image $M^2 I(x/M,y/M,R_2)$ of the obtained intensity distribution $I(x,y,R_2)$ is presented in FIG. 5. For comparison the calculated distribution of the phase Laplacian. $-\nabla^2\phi(x,y,0)$ was plotted as is shown in FIG. 6. Obviously, the scaled distribution of intensity on the image plane and the distribution of the Laplacian of the phase on the object plane appear almost identical, which supports formula (16) in the case of negligible absorption.

Figure 7:
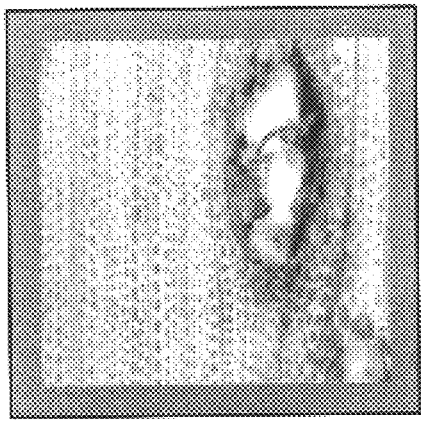
Figure 8:
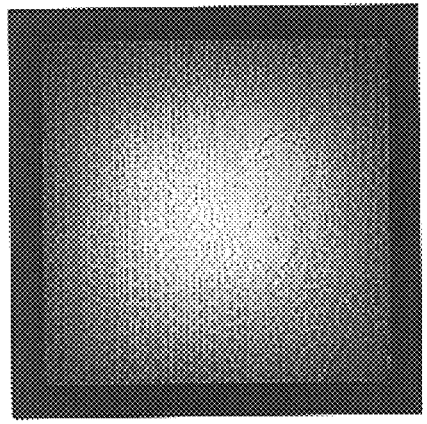

At the next stage the computed intensity distribution on the image plane and formula (20) were used to reconstruct the phase. The result of this reconstruction is shown in FIG. 7. Again, it is in a very good agreement with the original phase from FIG. 4, with the relative mean-square error of this reconstruction equal to 4.65%.

The performance of the method was also tested in the case of non-uniform intensity, i.e. when the last term in formula (16) was significant. As intensity distribution on the object plane was simulated according to the formula:

$I(x,y)=-1.647+3\times\exp\{-(x^2+y^2)/(2*1280^2)\}$.

Figure 9:
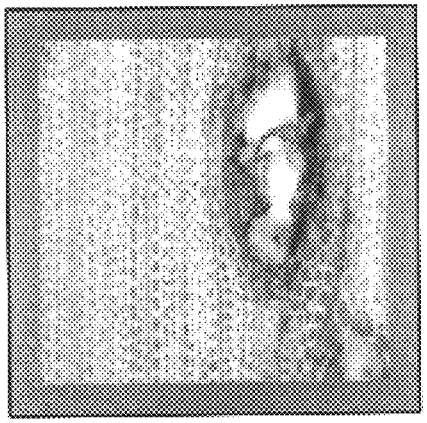

The values of the intensity had the range of [1, 1.1243]. The intensity distribution $I(x,y,R_2)$ on the image plane was computed by evaluating the Fresnel integrals. The non-uniformity of intensity distribution resulted in the "vignetting" of the corresponding image (FIG. 8), which clearly reflects the non-uniformity of intensity on the object plane. However, by subtracting the intensity distribution on the object plane from that on the image plane, dividing the difference by the scaled interplanar distance $R'=0.1$ m and applying formula (2) we were able to reconstruct the original phase with a root mean-square error of 6.67% (FIG. 9). This result confirms that in the case of moderate non-uniformity of intensity distribution on the object plane (e.g. weak absorption effects and/or weak uniformity of the incident beam), the described simple variation of formula (20) can be effectively used for quantitative retrieval of the phase shifts produced by the object.

EXAMPLE 2

Figure 10:
FIGS. 10 to 15 are photomicrographs depicting a test of an alternative approach.
Figure 11:
Figure 12:
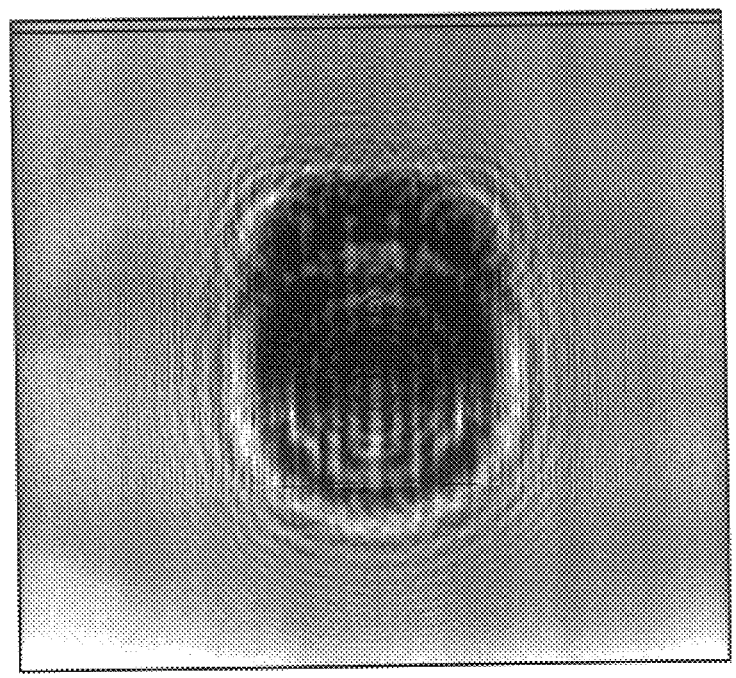
Figure 13:
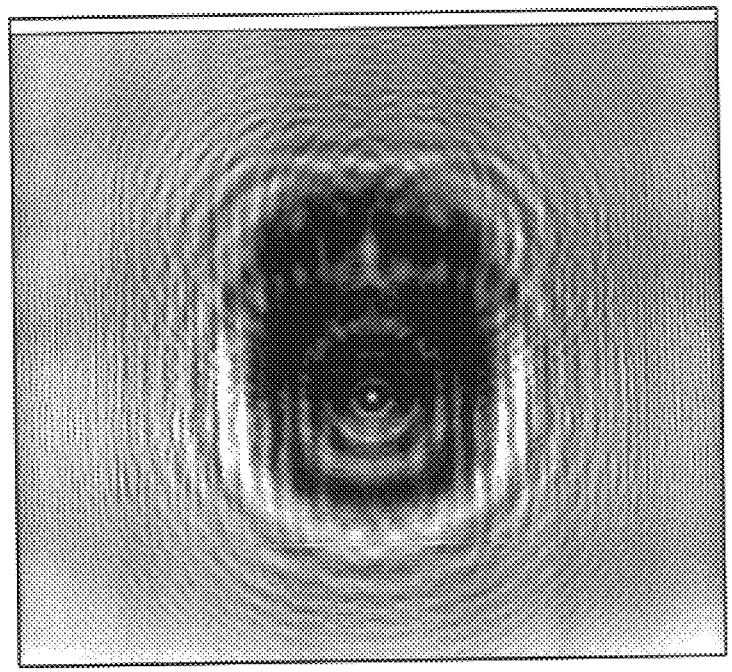
Figure 14:
Figure 15:
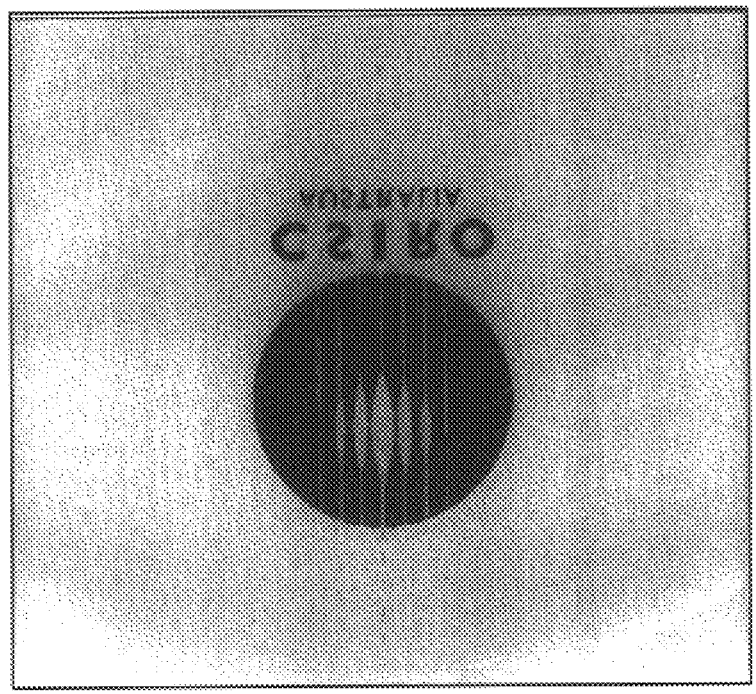

FIGS. 10 to 15 show an example of phase and absorption retrieval from tow images at different values of $R_2$. The CSIRO logo has been used as the absorption ($\mu$t) and phase ($\phi$t) distributions (FIGS. 10, 11 respectively). For the former the values are either 0.0 (black) or 0.1 (white), and for the latter (inverted logo) −0.1 (black) or 0.0 (white). The images (intensity distributions) were calculated for the plane-wave case, 1 Å radiation. 0.2×0.2 mm$^2$ (512×512 pixels) area, and $R_3=80$ cm (FIG. 12) and $R_2=106$ cm (FIG. 13). These conditions are such that the images are nit immediately interpretable. Applying the retrieval algorithm (44,45) discussed, we obtain the results shown (FIGS. 14, 15) which while not perfect, are clearly recognisable.

What is claimed is:

1. A method of obtaining an image of the phase change introduced by an object in penetrating radiation incident on the object, including:

irradiating the object with penetrating radiation having high lateral spatial coherence;

receiving at least a portion of said radiation at detector means after the radiation has emerged from the object and thereby obtaining and storing at least two intensity records for the received radiation each including intensity values at predetermined intervals; and utilising these values to derive a grid of values defining and image of the phase change introduced by the object in the penetrating radiation;

wherein said intensity records are obtained at a uniform finite distance after the radiation has emerged from the object, and are for respective different energy distributions of the detected radiation.

2. A method according to claim 1 wherein the respective different energy distributions are obtained by altering the energy spectrum of the radiation irradiating the object.

3. A method according to claim 1 wherein the respective different energy distributions are obtained by providing for said detector means to provide intensity as a function of energy in a certain energy band or band(s).

4. A method according to claim 1 wherein said derivation includes solving one or more differential transport-of-intensity equations relating the phase at a plane of the object to the evolution of the intensity distribution along the direction of propagation, utilising predetermined uniform boundary conditions.

5. A method according to claim 1 wherein said derivation includes solving Fourier-optics equations.

6. A method according to claim 1 wherein said intensity values also reflect absorption contrast in the object, and the method further includes utilising said values to derive a grid of values defining an effective pure absorption-contrast image of the object.

7. A method according to claim 1 wherein said penetrating radiation comprises x-ray radiation.

8. A method according to claim 7 wherein said x-ray radiation is in the range 0.5 KeV to 1 MeV.

9. A method according to claim 7 wherein said irradiating radiation is substantially monochromatic.

10. A method according to claim 7 wherein said irradiation radiation is polychromatic.

11. A method according to claim 7 wherein said irradiating radiation is from a substantially point source of full width half-maximum 40 µm or less.

12. Apparatus for obtaining an image of the phase change introduced by an object in penetrating radiation incident on the object, including:

means to provide a source for irradiating an object with penetration radiation having high lateral spatial coherence; and detector means for receiving at least a portion of said radiation after the radiation has emerged from the object whereby to generate at least two intensity records for the received radiation each including intensity values at predetermined intervals;

wherein said detector means is arranged for obtaining said intensity records at a uniform finite distance after the radiation has emerged from the object, and energy characterising means is provided whereby said intensity records are for respective different energy distributions of the detected radiation.

13. Apparatus according to claim 12 wherein said energy characterising means is arranged to alter the energy spectrum of the radiation irradiating the object.

14. Apparatus according to claim 13 wherein said energy characterising means includes means rendering the detector means able to provide intensity as a function of energy in a certain energy band or band(s).

15. Apparatus according to claim 12 further including a computer program product having a set of machine readable instructions which, when installed in a computer having a suitable operating system and memory means, configures the computer to be operable to utilise said values to derive a grid of values defining an image of the phase change introduced by the object in the penetrating radiation.

16. Apparatus according to claim 15 wherein said derivation includes solving one or more differential transport-of-intensity equations relating the phase at a plane of the object to the evolution of the intensity distribution along the direction of propagation, utilising predetermined uniform boundary conditions.

17. Apparatus according to claim 15 wherein said derivation includes solving Fourier-optics equations.

18. Apparatus according to claim 12 further including a source of x-ray radiation as said source for irradiating the object.

19. Apparatus according to claim 18 wherein said x-ray radiation is in the range of 0.5 KeV to 1 MeV.

20. Apparatus according to claim 18 wherein said irradiating radiation is substantially monochromatic.

21. Apparatus according to claim 18 wherein said irradiating radiation is polychromatic.

22. Apparatus according to claim 18 wherein said source is a substantially point source of full width half-maximum 40 µm or less.

23. A method of obtaining an image of the phase change introduced by an object in penetrating radiation incident on the object, from one or more two-dimensional intensity records of penetrating radiation after it has transversed the object, the radiation being of high lateral spatial coherence when incident on the object and the or each record being obtained at a finite distance after the radiation has emerged from the object incorporating phase-perturbed components within a surrounding field of radiation either uniformly phase-perturbed or not phase-perturbed, the method including:

storing intensity values from the or each record, at predetermined intervals;

utilising these values and any predetermined uniform boundary conditions to derive a grid of values defining an image of the phase change introduced by the object in the penetrating radiation, by solving a differential transport-of-intensity equation relating the phase at a plane at the object to the evolution of the intensity distribution along the direction of propagation.

24. A method according to claim 23 wherein said intensity values also reflect absorption contrast in the object, and the method further includes utilising said values to derive a grid of values defining an effective pure absorption-contrast image of the object.

25. A method according to claim 23 wherein said penetrating radiation comprises x-ray radiation.

26. A method according to claim 25 wherein said x-ray radiation is in the range 0.5 KeV to 1 MeV.

27. A method according to claim 25 wherein said irradiation radiation is substantially monochromatic.

28. A method according to claim 25 wherein said irradiating radiation is polychromatic.

29. A method according to claim 28 wherein said equation includes a spectrally weighted term of factor dependent on the square of the respective wavelength components.

30. A method according to claim 23 wherein said boundary conditions include uniform Dirichlet, Newmann or periodic boundary conditions, and are selected to achieve a unique solution of the equation for phase, at least up to and arbitrary constant component.

31. A method according to claim 30 wherein the solution further utilises one or more optical conditions selected from the group consisting of a small wavefront curvature for the incident radiation, absence of focal points between the object and image, and uniform illumination of the object.

32. Apparatus for obtaining an image of the phase change introduced by an object in penetrating radiation incident on the object, including:

a source for irradiation an object with penetrating radiation having high lateral spatial coherence;

a detector for receiving at least a portion of said radiation a finite distance after the radiation has emerged from the object incorporating phase-perturbed components within a surrounding field of radiation not phase-perturbed or uniformly phase-perturbed, whereby to generate intensity values for the received radiation at pre-determined intervals; and computer means, including a stored program of machine readable instructions, operable to utilise said values and any predetermined uniform boundary conditions to derive a grid of values defining and image of the phase change introduced by the object in the penetrating radiation, by solving a differential transport-of-intensity equation relating the phase at a plane at the object to the evolution of the intensity distribution along the direction of propagation.

33. A method of obtaining an image of the phase change introduced by an object in penetrating radiation incident of the object, including:

irradiating the object with penetrating radiation having high lateral spatial coherence;

receiving at least a portion of the said radiation at a detector at one or more finite distances after the radiation has emerged from the object incorporating phase-perturbed components within a surrounding field of radiation either uniformly phase-perturbed or not phase-perturbed, and thereby obtaining and storing intensity values for the received radiation at predetermined intervals; and utilising these values and any predetermined uniform boundary conditions to derive a grid of values defining and image of the phase change introduced by the object in the penetrating radiation, by solving a differential transport-of-intensity equation relating the phase at a plane at the object to the evolution of the intensity distribution along the direction of propagation.

34. A method according to claim 33 wherein said intensity values also reflect absorption contrast in the object, and the method further includes utilising said values to derive a grid of values defining and effective pure absorption-contrast image of the object.

35. A method according to claim 33 wherein said penetrating radiation comprises x-ray radiation.

36. A method according to claim 35 wherein said x-ray radiation is in the range 0.5 KeV to 1 MeV.

37. A method according to claim 35 wherein said irradiating radiation is substantially monochromatic.

38. A method according to claim 35 wherein said irradiating radiation is polychromatic.

39. A method according to claim 38 wherein said equation includes a spectrally weighted term or factor dependent on the square of the respective wavelength components.

40. A method according to claim 33 wherein said boundary conditions include uniform Dirichlet, Newmann or periodic boundary conditions, and are selected to achieve a unique solution of the equation for phase, at least up to and arbitrary constant component.

41. A method according to claim 40 wherein the solution further utilises one or more optical conditions selected from the group consisting of a small wavefront curvature for the incident radiation, absence of focal points between the object and image, and uniform illumination of the object.

* * * * *

UNITED STATES PATENT AND TRADEMARK OFFICE
CERTIFICATE OF CORRECTION

PATENT NO. : 6,226,353 B1
DATED : May 1, 2001
INVENTOR(S) : Stephen William Wilkins, et al.

It is certified that error appears in the above-identified patent and that said Letters Patent is hereby corrected as shown below:

Title page, ABSTRACT,
Line 1, change "in", to read -- an --.

Column 8,
Equation (3), line 26, change "$z^3$", to read -- $z^2$ --.
Equation (5), change "1-n+m)", to read -- 1-(n+m) --.
Equation (6), change "and $| \partial y^m$", to read -- and $| \partial xm\ \partial yn$ --.

Column 12,
Equation (21), change "$\int$", to read -- $\int_{-\infty}^{\infty}$ --.

Column 14,
Line 66, change "$", to read -- R --.

Column 16,
Equation (39), change "9$f_x, f_y$)", to read -- ($f_x, f_y$) --.

Signed and Sealed this

Eighteenth Day of September, 2001

Attest:

NICHOLAS P. GODICI
*Attesting Officer*    *Acting Director of the United States Patent and Trademark Office*